United States Patent
Benov et al.

(10) Patent No.: US 9,034,596 B1
(45) Date of Patent: May 19, 2015

(54) METHOD FOR FLUORESCENT STAINING OF CELLULAR AND INTRACELLULAR MEMBRANES

(71) Applicants: Ludmil Tzvetanov Benov, Jabriya (KW); Rima Abdul Ghani Ezzeddine, Al-Yarmook (KW); Anwar Gh. A. Gh. Albanaw, Yarmouk (KW); Ines Batinic-Haberle, Durham, NC (US); James D. Craik, Shuwaikh (KW); Artak Tovmasyan, Durham, NC (US)

(72) Inventors: Ludmil Tzvetanov Benov, Jabriya (KW); Rima Abdul Ghani Ezzeddine, Al-Yarmook (KW); Anwar Gh. A. Gh. Albanaw, Yarmouk (KW); Ines Batinic-Haberle, Durham, NC (US); James D. Craik, Shuwaikh (KW); Artak Tovmasyan, Durham, NC (US)

(73) Assignee: KUWAIT UNIVERSITY, Safat (KW)

( * ) Notice: Subject to any disclaimer, the term of this patent is extended or adjusted under 35 U.S.C. 154(b) by 0 days.

(21) Appl. No.: 14/255,929

(22) Filed: Apr. 17, 2014

(51) Int. Cl.
*A61K 49/00* (2006.01)
*G01N 1/30* (2006.01)

(52) U.S. Cl.
CPC ............ *G01N 1/30* (2013.01); *G01N 2001/302* (2013.01)

(58) Field of Classification Search
IPC ............................ A61K 49/0032; G01N 33/582
See application file for complete search history.

(56) References Cited

U.S. PATENT DOCUMENTS

| | | | |
|---|---|---|---|
| 4,614,723 A | | 9/1986 | Schmidt et al. |
| 4,937,198 A | | 6/1990 | Lee et al. |
| 5,236,902 A | * | 8/1993 | Paterson et al. ................. 514/24 |
| RE35,904 E | * | 9/1998 | Paterson et al. ................. 514/24 |
| 6,291,203 B1 | | 9/2001 | Poot et al. |
| 7,432,369 B2 | | 10/2008 | Williams et al. |
| 7,485,721 B2 | | 2/2009 | Batinic-Haberle et al. |
| 2006/0193780 A1 | | 8/2006 | Gray |
| 2006/0223125 A1 | | 10/2006 | Lelkes et al. |

FOREIGN PATENT DOCUMENTS

| CN | 1715919 | 1/2006 |
|---|---|---|
| WO | WO 2012/099317 | 7/2012 |

OTHER PUBLICATIONS

Ezzeddine R. et al. Effect of Molecular Characteristics on Cellular Uptake . . . J of Biological Chemistry 288(51)36579-36588, Dec. 20, 2013.*
Amao Y. et al. Photoinduced Hydrogen Evolution with Hydrogenase and Water Soluble Viologen Linked Zinc Porphyrins. J of Porphyrins and Phthalocyanines 2(3)201-207, 1998.*
Amao Y. et al. Synthesis and Characterization of Water Soluble Viologen Linked Zinc Porphyrins. J of Photochemistry Photobiology A: Chemistry. 98(1-2)59-64, Aug. 1996.*
Zhang et al., "Water-Soluble Prophyrins as a Dual Function Molecular Imaging Platform for MRI and Fluorescence Zinc Sensing," PNAS, Jun. 19, 2007.
Benov et al., "Isomeric N-alkylpyridylporphyrins and their Zn(II) complexes: inactive as SOD mimics but powerful photosensitizers", Archives of Biochemistry and Biophysics, vol. 402, (2002), pp. 159-165.

* cited by examiner

*Primary Examiner* — Ralph Gitomer
(74) *Attorney, Agent, or Firm* — Richard C Litman

(57) ABSTRACT

The method for fluorescent staining of cellular and intracellular membranes includes contacting a cell sample, such as a cell culture, with a fluorescent probe including Zn(II) meso-tetrakis(N-n-hexylpyridinium-4-yl)porphyrin tetrachloride (ZnTnHex-4-PyPCl$_4$). The fluorescent probe is an amphiphilic, water-soluble compound. The fluorescent probe does not interfere with cell culture media components or other staining products. The fluorescent probe is not harmful to cells.

12 Claims, 2 Drawing Sheets

METHOD FOR FLUORESCENT STAINING OF CELLULAR AND INTRACELLULAR MEMBRANES

BACKGROUND OF THE INVENTION

1. Field of the Invention

The present invention relates to methods for staining membranes, and particularly to a method for fluorescent staining of cellular and intracellular membranes for visualization in confocal microscopy and other fluorescent microscopy techniques.

2. Description of the Related Art

Fluorescent dyes or stains are extremely useful for biological applications based on highly sensitive detection procedures. For example, fluorescent stains are useful in confocal and other fluorescent microscopy techniques for visualization of cells, cellular organelles and tissues. Fluorescent staining allows researchers to observe cellular structures and to monitor physiological and pathological changes. In addition, fluorescent staining allows cell sorting by the use of flow cytometry or other analytical techniques.

Many of the most commonly used methods of fluorescent staining of cells require use of fluorescent dyes having characteristics that interfere with their utility. For example, many fluorescent dyes do not provide high fluorescence intensity and/or are unstable in aqueous environments.

Thus, a method for fluorescent staining of cellular and intracellular membranes is desired.

SUMMARY OF THE INVENTION

The method for fluorescent staining of cellular and intracellular membranes includes contacting a cell sample, such as a cell culture, with a fluorescent probe including Zn(II) meso-tetrakis(N-n-hexylpyridinium-4-yl)porphyrin tetrachloride (ZnTnHex-4-PyCl$_4$). The fluorescent probe is an amphiphilic, ater-soluble compound. The fluorescent probe does not interfere with cell culture media components or other staining products. The fluorescent probe is not harmful to cells.

These and other features of the present invention will become readily apparent upon further review of the following specification and drawings.

BRIEF DESCRIPTION OF THE DRAWINGS

Similar reference characters denote corresponding features consistently throughout the attached drawings.

Figure 1:
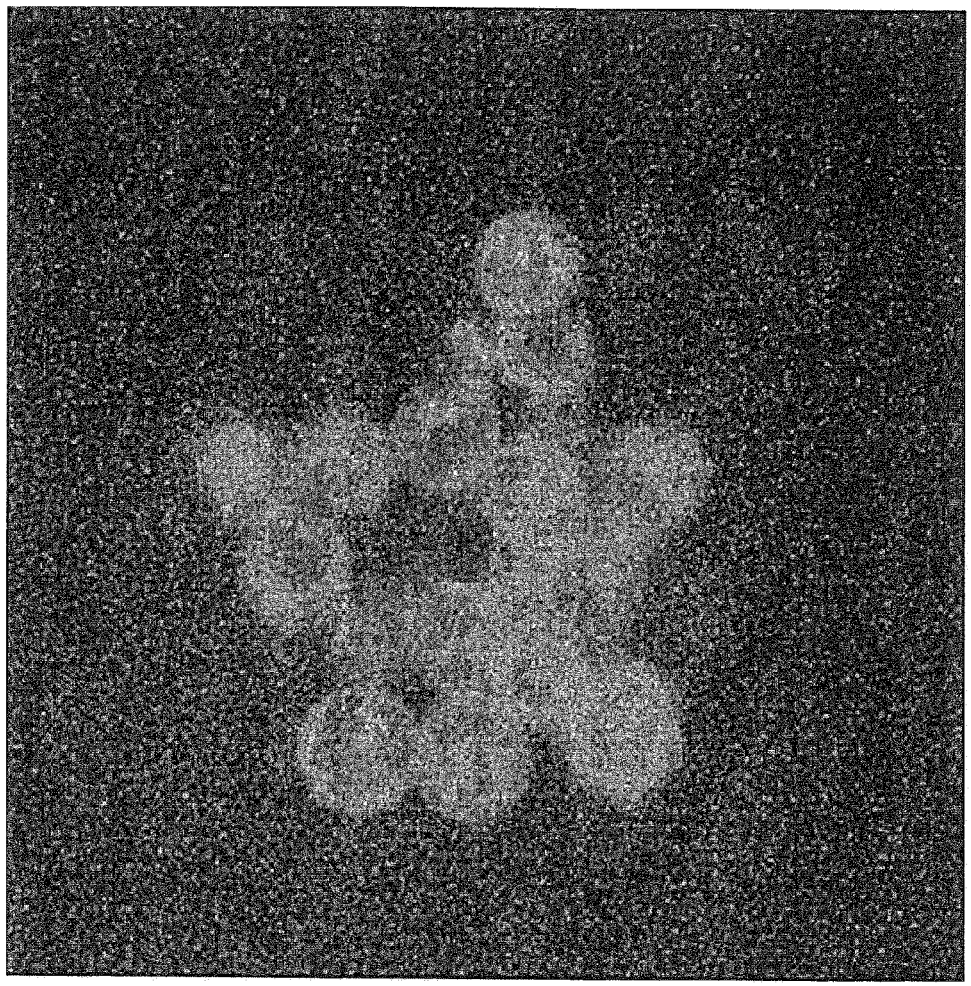
FIG. 1 is a micrograph showing a confocal microscopy image obtained after cancer cells were incubated with the fluorescent probe (15 min, 1 μM).

The method for fluorescent staining of cellular and intracellular membranes includes contacting a cell sample, such as a cell culture, with a fluorescent probe including Zn(II) meso-tetrakis(N-n-hexylpyridinium-4-yl)porphyrin tetrachloride (ZnTnHex-4-PyCl$_4$). The structural formula for Zn(II) meso-tetrakis(N-n-hexylpyridinium-4-yl)porphyrin tetrachloride (ZnTnHex-4-PyCl$_4$) is provided below:

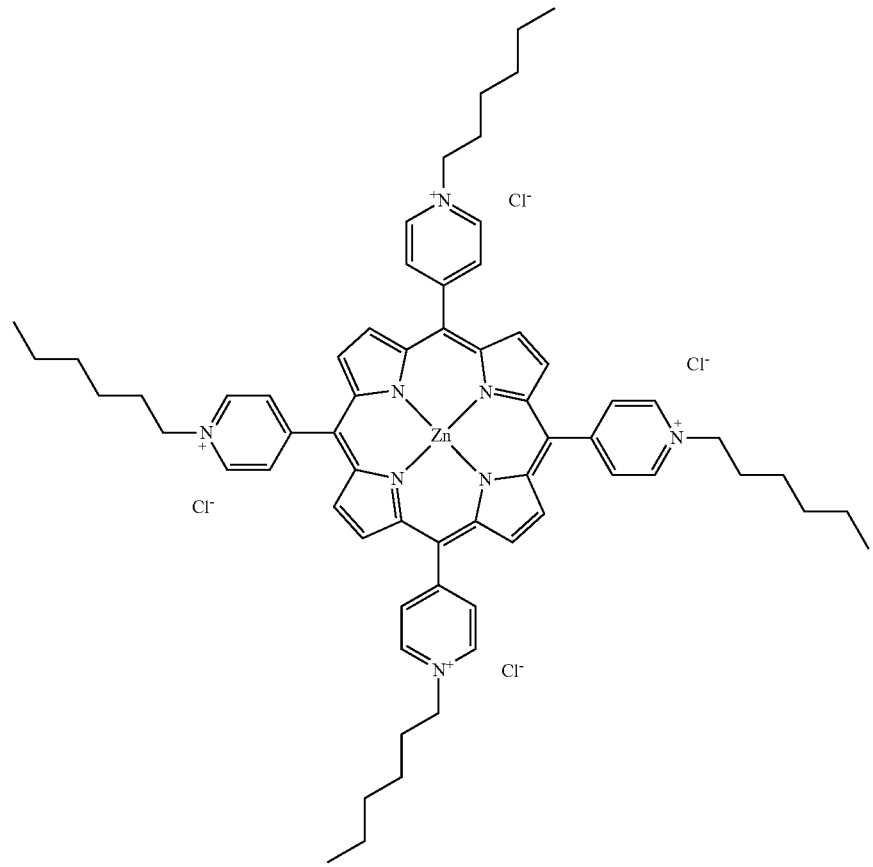

Contacting the cell sample with the fluorescent probe may be achieved by adding the fluorescent probe to the cell sample. For example, a cell culture may be grown and the fluorescent probe may be directly added to the cell culture. The fluorescent probe may be added to the cell culture at any time of cell growth. The cells may be washed after fixation and mounted on slides for examination using a confocal fluorescence microscope, for example.

As stated above, the fluorescent probe may be incubated with a cell culture. The fluorescent probe may be added to the cell culture at any time during growth of the culture. During incubation of the fluorescent probe with the cell culture, the fluorescent probe may be retained in cellular and/or intracellular membranes of the cells in the cell culture. The fluorescent probe may remain in the cellular and intra-cellular membranes during cell fixation and washing. In this manner, cellular membrane and intracellular membrane structures may be selectively stained.

The fluorescent probe may be retained long enough in the cellular and/or intracellular membranes to produce a fluorescent emission that allows visualization and ultimately, sorting of subgroups of cells. The fluorescent probe may produce a fluorescent emission without harming cells. For example, the fluorescent probe may produce a fluorescent emission that highly exceeds autofluorescence without harming cells. The fluorescent probe may produce a fluorescent emission without interfering with media components.

The fluorescent probe may be an amphiphilic compound, and soluble in water, physiological saline, and any media used for growing cell cultures. The fluorescent probe may be used in a cell culture without affecting cell growth. The fluorescent probe may selectively stain cellular membranous structures in living cells. For example, the fluorescent probe may selectively stain cellular and intracellular membranes and organelles that contain lipid-based structures.

The fluorescent probe may include Zn(II) meso-tetrakis(N-n-hexylpyridinium-4-yl)porphyrin tetrachloride (ZnTnHex-4-PyPCl$_4$), which is a water soluble compound. Zn(II) meso-tetrakis(N-n-hexylyridinum-4-yl)porphyrin includes a positively charged (4+) tetrapyrrole porphyrin ring compound and four pyridyl groups extending from the tetrapyrrole porphyrin ring. The positively charged (4+) tetrapyrrole porphyrin ring compound possesses amphiphilic properties, making the fluorescent probe both soluble in water and soluble in a lipid membrane bilayer. The four positive charges of the tetrapyrrole porphyrin ring may contribute to the electrostatic attraction of the fluorescent probe to negatively charged membrane components and to asymmetric distribution of charges in a negatively charged organelle interior, e.g., the mitochondrial interior. The four pyridyl groups extending from the tetrapyrrole porphyrin ring are each attached to alkyl chains. The alkyl chains are attached to the meso pyridyl nitrogen in the para position and preferably include six carbon atoms. The alkyl chains provide sufficient hydrophobicity without limiting solubility.

The fluorescent probe may be used without interfering with other staining procedures or fluorescent dyes. For example, a cell culture may be incubated concurrently with the fluorescent probe and other staining products or fluorescent dyes. The fluorescent probe may successfully be used with other known staining products, such as MITOTRACKER GREEN FM, LYSOSENSOR GREEN DND-189, DIOC6(3) IODIDE, and BODIPY-CERAMIDE.

The concentration of the fluorescent probe added to a cell culture may depend upon the required fluorescence intensity of dye sufficient. Generally, a concentration of at least 0.5-1 µM of the fluorescent probe may be needed for staining membranes in living mammalian cells. At such concentrations, the fluorescent probe may stain cellular and intracellular membranes in a short amount of time and produce a fluorescent emission. For example, concentrations as low as about 0.5-2.5 µM of the fluorescent probe may stain cellular and intracellular membranes within 15 minutes. FIG. 1 shows a confocal microscopy image of cancer cells that were incubated with 0.5 µM of the fluorescent probe for 15 minutes.

Figure 2:
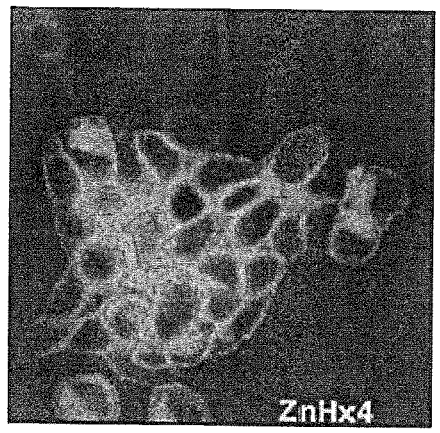
FIG. 2 is a micrograph showing a confocal microscopy image showing subcellular localization of the fluorescent probe in LS174 T cells at 20 μM (40× magnification) after 24 hours of preincubation in the dark.
Figure 3:
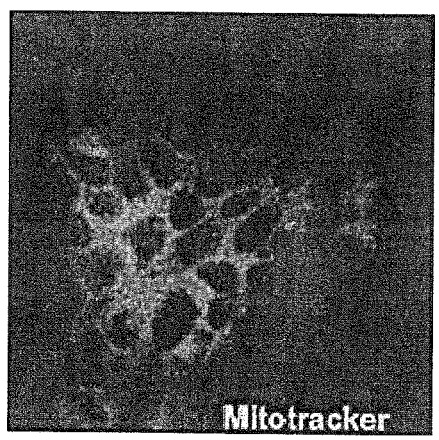
FIG. 3 is a micrograph showing a confocal microscopy image showing co-localization of Mitotracker Green FM in LS174 T cells.
Figure 4:
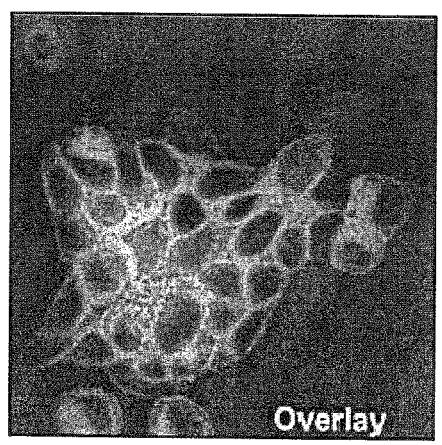
FIG. 4 is a micrograph showing a confocal microscopy image showing an overlay image of FIGS. 2 and 3.

Greater concentrations of the fluorescent probe may also be used without harming cells. It should be understood, however, that it may be necessary to shield the fluorescent probe from light to avoid harming the cells. For example, a 20 µM concentration of the fluorescent probe may be used without harming cells. FIG. 2 shows a confocal microscopy image of subcellular localization of the fluorescent probe in LSI74T cells (localization of the fluorescent probe in mitochondria, lysosomes, the ER and the plasma membrane) at 20 µM after 24 hours of pre-incubation in the dark. A high concentration of the fluorescent probe also does not interfere with other fluorescent staining products. FIG. 3 shows co-localization of the fluorescent probe with MITOTRACKER GREEN in LSI74T cells. FIG. 4 shows an overlay of the images shown in FIGS. 2 and 3.

As discussed above, the fluorescent probe may be introduced to physiological saline, cell culture media and other cell-culture compatible solutions. As the fluorescent probe is water soluble, the use of hydrophobic, cell-harming and toxic organic solvents may be avoided. The fluorescent probe may be easily sterilized by filtration through a sterilization filter, for example, a 0.2 µm sterilization filter. The fluorescent probe may be sterilized and kept for months refrigerated in the dark. Fluorescent staining does not require any additional procedure because the fluorescent probe may directly be added or included in the growth medium.

EXAMPLE 1

Synthesis of Zn(II) meso-tetrakis(N-n-hexylpyridinium-4-yl)porphyrin tetrachloride (ZnTnHex-4-PyPCl4)

Synthesis of Zn(II) meso-tetrakis(N-n-hexylpyridinium-4-yl)porphyrin tetrachloride (ZnTnHex-4-PyPCl$_4$) was performed as described by Benov et al. (*Arch. Biochem. Biophys.* 2002, 402: 159), hereby incorporated by reference in its entirety. Elemental analysis: ZnTnHex-4-PyPCl$_4 \times$(H$_2$O)$_9$: Anal. Calcd for C$_{64}$H$_{94}$Cl$_4$N$_8$ZnO$_9$: H, 7.14; C, 57.94; N, 8.45%. Found: H, 6.61; C, 57.71; N, 8.42%, Uv-Vis, $\lambda_{max}$, nm (log $\epsilon$, M$^{-1}$ cm$^{-1}$): 216.0 (4.64), 259.5 (4.47), 325.5 (4.45), 438.0 (5.40), 565.0 (4.33), 606.5 (3.87).

Stock solutions of ZnTnHex-4-PyPCl$_4$ can be prepared in distilled water, PBS, or cell culture media.

EXAMPLE 2

Cell Membrane Staining

Monolayer cultures were grown in RPMI 1640 medium (Gibco) supplemented with 10% fetal bovine serum (FBS) (Gibco), 1% L-glutamine (Gibco), 1% penicillin/streptomycin (Gibco) as an antibacterial agent and 0.1% amphotericin (Sigma) as an antifungal agent. The cultures were maintained at 37° C. in a CO$_2$ incubator with humidified atmosphere, 5% CO$_2$ and 95% air. Confluent cultures (80-90%) were used for experiments. The cells were then detached by trypsinization and incubation at 37° C. for 2-3 minutes. Fresh medium (10× to trypsin's volume) was added to inhibit trypsin action. The cell suspension was centrifuged at 500 g for three minutes. The supernatant was discarded and the pellet obtained was resuspended in fresh medium. Cells were counted and seeded onto sterile glass cover slips at $5 \times 10^4$ cells per slip and incubated overnight to adhere. ZnTnHex-4-PyPCl$_4$ was added and the cells were incubated with the compound in the dark. The cells were then fixed with ice cold absolute ethanol added to a final concentration of 60%, and the plate containing the slips was kept on ice for 10 minutes. The cells were washed with PBS twice and the slips were transferred onto microscopic slides. Vectashield mounting medium from Vector Laboratories was used. The slides were examined using a Zeiss LSM 510 META confocal fluorescence microscope fitted with standard FITC, Rhodamine and DAPI filter sets.

EXAMPLE 3

Cell Membrane Staining

LS174T cells were counted and seeded onto sterile glass cover slips at $5 \times 10^4$ cells per slip and incubated over-night to adhere. The dye was added to a final concentration of 0.5-2.5 µM and the cells were incubated with ZnTnHex-4-PyPCl$_4$ in the dark for 15-30 minutes. The cells were then fixed with ice cold absolute ethanol added to a final concentration of 60%, and the plate containing the slips was kept on ice for 10 minutes. The cells were washed with PBS twice and the slips were transferred onto microscopic slides. Vectashield mounting medium from Vector Laboratories was used. The slides were examined using a Zeiss LSM 510 META confocal fluorescence microscope fitted with standard FITC, Rhodamine and DAPI filter sets.

It is to be understood that the present invention is not limited to the embodiments described above, but encompasses any and all embodiments within the scope of the following claims.

We claim:

1. A method for fluorescent staining of cellular and intracellular membranes, comprising the step of contacting a cell sample with a fluorescent probe, the fluorescent probe comprising Zn(II) meso-tetrakis(N-n-hexylpyridinium-4-yl)porphyrin tetrachloride (ZnTnHex-4-PyPCl$_4$).

2. The method for fluorescent staining of cellular and intracellular membranes of claim 1, further comprising the step of washing the cell sample.

3. The method for fluorescent staining of cellular and intracellular membranes of claim 1, further comprising the step of viewing the stained sample with a confocal fluorescent microscope.

4. The method for fluorescent staining of cellular and intracellular membranes of claim 1, wherein the cell sample includes a cell culture.

5. The method for fluorescent staining of cellular and intracellular membranes of claim 1, wherein the fluorescent probe is water soluble.

6. The method for fluorescent staining of cellular and intracellular membranes of claim 1, wherein the fluorescent probe is amphiphilic.

7. The method for fluorescent staining of cellular and intracellular membranes of claim 1, further comprising contacting the cell sample with a staining product, the staining product being different from the fluorescent probe.

8. The method for fluorescent staining of cellular and intracellular membranes according to claim 1, further comprising the step of incubating the fluorescent probe and the cell sample in the dark.

9. A method for fluorescent staining of cellular and intracellular membranes, comprising the steps of:
    growing a cell culture;
    contacting the cell culture with a fluorescent probe, the fluorescent probe including Zn(II) meso-tetrakis(N-n-hexylpyridinium-4-yl)porphyrin tetrachloride (ZnTnHex-4-PyPCl4);
    washing the cell culture after contacting the cell culture with the fluorescent probe; and
    retaining the fluorescent probe in cellular membranes of cells in the cell sample after washing the cell sample.

10. The method for fluorescent staining of cellular and intracellular membranes of claim 9, wherein the fluorescent probe is water soluble.

11. The method for fluorescent staining of cellular and intracellular membranes of claim 9, wherein the fluorescent probe is amphiphilic.

12. The method for fluorescent staining of cellular and intracellular membranes of claim 9, further comprising the contacting the cell culture with a staining product, the staining product being different from the fluorescent probe.

* * * * *